United States Patent
Long et al.

(10) Patent No.: US 11,364,334 B2
(45) Date of Patent: Jun. 21, 2022

(54) SYSTEM AND METHOD FOR UTILIZING PRESSURE DECAY TO DETERMINE AVAILABLE FLUID CAPACITY IN A NEGATIVE PRESSURE DRESSING

(71) Applicant: KCI LICENSING, INC., San Antonio, TX (US)

(72) Inventors: Justin A. Long, Bournemouth (GB); Benjamin A. Pratt, Poole (GB)

(73) Assignee: KCI Licensing, Inc., San Antonio, TX (US)

(*) Notice: Subject to any disclaimer, the term of this patent is extended or adjusted under 35 U.S.C. 154(b) by 292 days.

(21) Appl. No.: 16/363,810

(22) Filed: Mar. 25, 2019

(65) Prior Publication Data

US 2020/0061253 A1 Feb. 27, 2020

Related U.S. Application Data

(60) Provisional application No. 62/720,788, filed on Aug. 21, 2018.

(51) Int. Cl.
*A61M 1/00* (2006.01)
*A61F 13/00* (2006.01)
*A61F 13/02* (2006.01)

(52) U.S. Cl.
CPC ....... *A61M 1/962* (2021.05); *A61F 13/00068* (2013.01); *A61M 1/73* (2021.05);
(Continued)

(58) Field of Classification Search
CPC .......... A61M 1/90; A61M 1/73; A61M 1/734; A61M 2205/15; A61M 2205/3344;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

International Search Report and Written Opinion in International Application No. PCT/US2019/023912, dated Jun. 3, 2019.
(Continued)

*Primary Examiner* — Kai H Weng
*Assistant Examiner* — Seth Han

(57) ABSTRACT

A negative pressure wound therapy system includes at least one sensor coupled to a wound dressing for a wound of a patient, and a processing circuit. The at least one sensor is configured to output a measurement of the pressure in the wound dressing. The processing circuit is configured to open a sealable aperture, receive the pressure measurements in the wound dressing, calculate a rate of pressure decay, correlate the rate of pressure decay in the wound dressing to a wound dressing fluid absorbent capacity and other therapy parameters, and output the wound dressing fluid absorbent capacity and other therapy parameters to a remote electronic device.

33 Claims, 11 Drawing Sheets

(52) U.S. Cl.
CPC ............ *A61M 1/74* (2021.05); *A61F 13/0216* (2013.01); *A61M 2205/3344* (2013.01)

(58) Field of Classification Search
CPC .. A61M 2205/3331; A61M 2001/0068; A61M 2205/3334; A61M 1/0025; A61M 1/0031; A61M 1/0088; A61M 1/009; A61M 1/0092; A61M 2205/18; A61M 2205/3379; A61F 13/00068; A61F 13/0216
USPC ....................................................... 604/6.06
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,348,595 B2 | 3/2008 | Takeoka et al. |
| 8,114,126 B2 | 2/2012 | Heaton et al. |
| 8,142,419 B2 | 3/2012 | Heaton et al. |
| 8,192,409 B2 | 6/2012 | Hardman et al. |
| 8,197,467 B2 | 6/2012 | Heaton et al. |
| 8,608,776 B2 | 12/2013 | Coward et al. |
| 8,814,841 B2 | 8/2014 | Hartwell |
| 8,936,618 B2 | 1/2015 | Sealy et al. |
| 9,050,208 B2 | 6/2015 | Locke et al. |
| 9,192,332 B2 | 11/2015 | Hartwell |
| 9,408,954 B2 * | 8/2016 | Gordon ............... A61M 1/0001 |
| 9,757,500 B2 | 9/2017 | Locke et al. |
| 9,844,485 B2 * | 12/2017 | Locke .................. A61N 1/0468 |
| 9,987,402 B2 | 6/2018 | Hartwell |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2007/0276195 A1 | 11/2007 | Xu et al. |
| 2007/0276309 A1 | 11/2007 | Xu et al. |
| 2008/0071161 A1 | 3/2008 | Jaeb et al. |
| 2009/0030383 A1 | 1/2009 | Larsen et al. |
| 2011/0213319 A1 | 9/2011 | Blott et al. |
| 2014/0066868 A1 | 3/2014 | Freedman et al. |
| 2015/0165182 A1* | 6/2015 | Pratt ..................... A61M 37/00 604/290 |
| 2015/0231314 A1* | 8/2015 | Robinson .......... A61F 13/00017 604/319 |
| 2015/0320603 A1 | 11/2015 | Locke et al. |
| 2016/0045648 A1 | 2/2016 | Locke et al. |
| 2016/0166740 A1 | 6/2016 | Hartwell |
| 2017/0007752 A1 | 1/2017 | Freedman et al. |
| 2017/0209641 A1 | 7/2017 | Mercer et al. |
| 2017/0216501 A1* | 8/2017 | Armstrong ............ A61M 1/90 |
| 2017/0319761 A1 | 11/2017 | Locke et al. |

(56) References Cited

U.S. PATENT DOCUMENTS

2018/0055977 A1 3/2018 Pratt et al.
2018/0369456 A1 12/2018 Hartwell

FOREIGN PATENT DOCUMENTS

| AU | 755496 B2 | 12/2002 | |
|---|---|---|---|
| CA | 2005436 A1 | 6/1990 | |
| DE | 26 40 413 A1 | 3/1978 | |
| DE | 43 06 478 A1 | 9/1994 | |
| DE | 29 504 378 U1 | 9/1995 | |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 1018967 A1 | 7/2000 | |
| EP | 2 237 724 A1 | 10/2010 | |
| EP | 3 269 404 A1 | 1/2018 | |
| GB | 692578 A | 6/1953 | |
| GB | 2 004 942 A | 4/1979 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/020041 A1 | 9/1994 | |
| WO | 96/05873 A1 | 2/1996 | |
| WO | 97/18007 A1 | 5/1997 | |
| WO | 99/13793 A1 | 3/1999 | |
| WO | WO-2005/105175 A1 | 11/2005 | |
| WO | WO-2007/030601 A2 | 3/2007 | |
| WO | WO-2010/093753 A1 | 8/2010 | |
| WO | WO-2012/106590 A2 | 8/2012 | |
| WO | WO-2013/066694 A2 | 5/2013 | |
| WO | WO-2013/175309 A1 | 11/2013 | |
| WO | WO-2015/110409 A1 | 7/2015 | |
| WO | WO-2015/110410 A1 | 7/2015 | |
| WO | WO-2016/176513 A1 | 11/2016 | |
| WO | WO-2017/087687 A1 | 5/2017 | |
| WO | WO-2018/005330 A1 | 1/2018 | |
| WO | WO-2018/013242 A1 | 1/2018 | |
| WO | WO-2018013242 A1 * | 1/2018 | ....... A61F 13/00068 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Bjorn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

(56) References Cited

OTHER PUBLICATIONS

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

\* cited by examiner

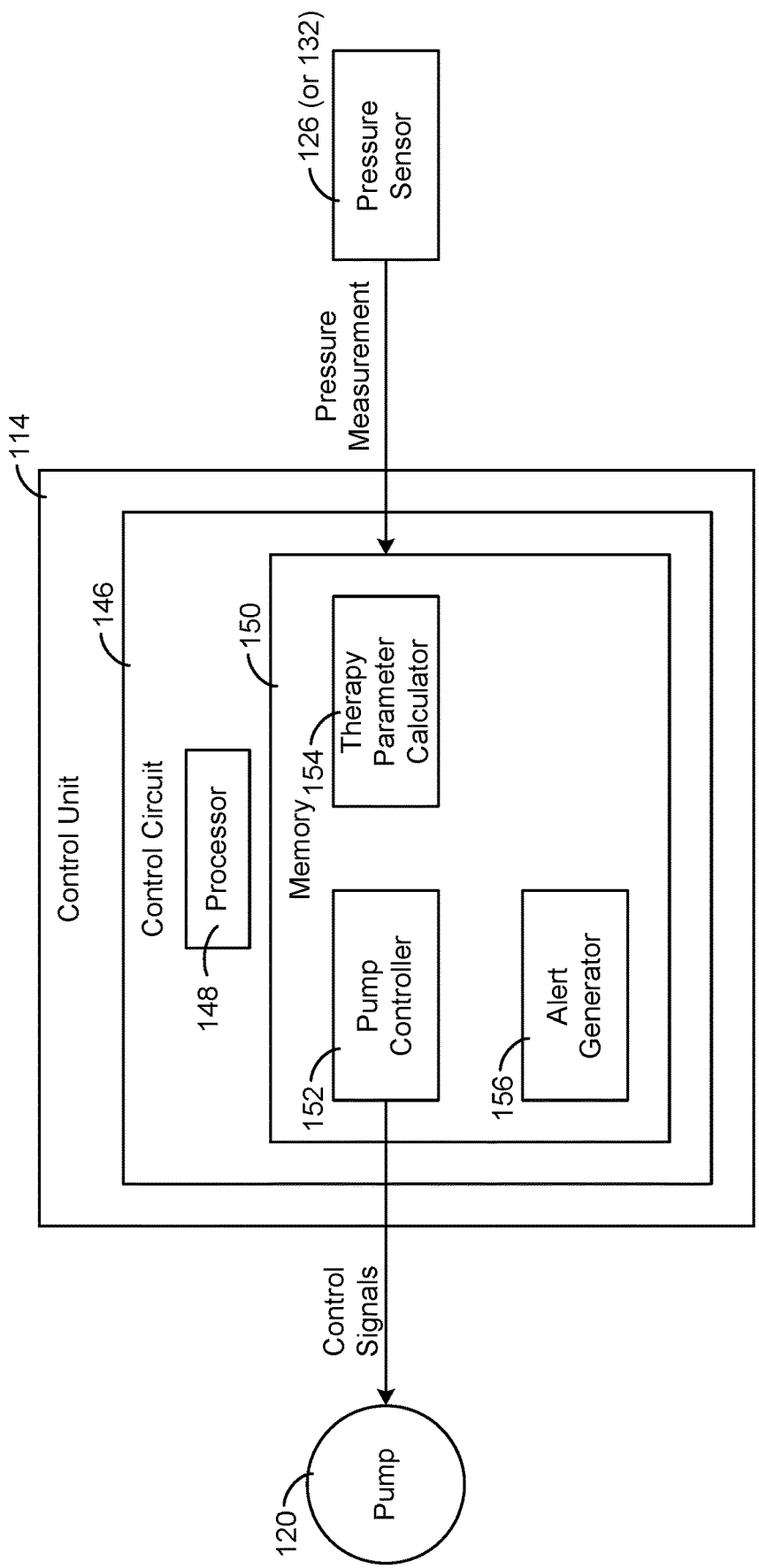

SYSTEM AND METHOD FOR UTILIZING PRESSURE DECAY TO DETERMINE AVAILABLE FLUID CAPACITY IN A NEGATIVE PRESSURE DRESSING

CROSS-REFERENCE TO RELATED APPLICATIONS

This application claims the benefit of priority to U.S. Provisional Application No. 62/720,788, filed on Aug. 21, 2018, which is incorporated herein by reference in its entirety.

BACKGROUND

The present disclosure relates generally to wound therapy systems and devices, and more particularly to systems and methods for utilizing pressure decay rates to determine the available fluid capacity in a negative pressure dressing.

Negative pressure wound therapy (NPWT) is a type of wound therapy that involves applying negative pressure (relative to atmosphere pressure) to a wound site, via a wound dressing, to promote wound healing. Some NPWT systems include a pump which operates to maintain the wound site at negative pressure by removing wound exudate from the wound site via the wound dressing.

SUMMARY

One implementation of the present disclosure is a negative pressure wound therapy system. The negative would pressure system includes at least one sensor coupled to a wound dressing for a wound of a patient, a sealable aperture coupled to the at least one sensor, a processing circuit, and a communications circuit. The at least one sensor is configured to detect a pressure in the wound dressing. The processing circuit is configured to open the sealable aperture to induce a pressure change between the pressure in the wound dressing and atmospheric pressure, calculate a rate a pressure decay in the wound dressing corresponding to the pressure change, and calculate a wound dressing fluid absorbent capacity based on the rate of pressure decay. The communications circuit is coupled to the processing circuit and is configured to transmit data to a remote electronic device. This data can include the rate of pressure decay and/or the wound dressing fluid absorbent capacity.

In some embodiments, the processing circuit is configured to open the sealable aperture to calculate the wound dressing fluid absorbent capacity at start up. The control unit can be configured to store the pressure change measured by the sensor over time. The processing circuit can calculate and store the rate of pressure decay based on the stored pressure change over time. After obtaining the rate of pressure decay, the processing circuit can calculate the wound dressing fluid absorbent capacity based on the rate of pressure decay.

In some embodiments, the communications circuit is further configured to transmit the wound dressing fluid absorbent capacity to the remote electronic device responsive to at least one of either an expiration of a predetermined time interval or a request.

In some embodiments, the processing circuit is further configured to compare the wound dressing fluid absorbent capacity to a predetermined threshold condition including at least one of a minimum threshold or maximum threshold. The processing circuit can output an alert to the remote electronic device responsive to the wound dressing fluid absorbent capacity not satisfying the designated predetermined threshold condition.

In some embodiments, the processing circuit is configured to calculate an exudate volume in the wound dressing based on the wound dressing fluid absorbent capacity.

In some embodiments, the communications circuit is configured to transmit the exudate volume in the wound dressing to the remote electronic device responsive to at least one of either an expiration of a predetermined time interval or a request.

In some embodiments, the processing circuit is configured to calculate a wound to dressing fluid absorbance rate based on the wound dressing fluid capacity.

In some embodiments, the communications circuit is configured to transmit the wound to dressing fluid absorbance rate to the remote electronic device responsive to at least one of either an expiration of a predetermined time interval or a request.

In some embodiments, the processing circuit is configured to open the sealable aperture responsive to at least one of an expiration of one or more predetermined time intervals subsequent to start up, or detecting a pressure change greater than a threshold pressure change.

In some embodiments, the processing circuit is configured to calculate, each time the sealable aperture is opened, an updated rate of pressure decay and an updated wound dressing fluid absorbent capacity.

In some embodiments, the processing circuit is configured to compare the updated wound dressing fluid absorbent capacity to a predetermined threshold condition including at least one of a minimum threshold or maximum threshold. The processing circuit can output an alert to the remote electronic device responsive to the updated wound dressing fluid absorbent capacity not satisfying the predetermined threshold condition.

In some embodiments, the processing circuit is configured to calculate an updated exudate volume in the wound dressing and/or an updated wound to dressing fluid absorbent rate based on the updated wound dressing fluid absorbent capacity.

In some embodiments, the wound dressing is an incisional wound dressing for placement over a closed incision.

In some embodiments, the wound dressing includes a lower, wound facing layer, an absorbent core, and a cover layer for sealing the dressing to a patient's skin.

In some embodiments, the at least one sensor is coupled to the processing circuit and mounted in a therapy unit.

In some embodiments, the sealable aperture consists of a two-way controllable exhaust valve.

In some embodiments, the sealable aperture consists of a controllable pump containing an internal leak.

Another implementation of the present disclosure is a method. The method includes detecting, by at least one sensor of a therapy unit, a pressure in a wound dressing and opening, by the processing circuit, a sealable aperture responsive to at least one of (1) start up, (2) expiration of one or more predetermined time intervals subsequent to start up, or (3) detecting a pressure change greater than a threshold pressure change, to induce a pressure change based on the pressure in the wound dressing to atmospheric pressure. The method includes calculating, by the processing circuit, a rate of pressure decay in the wound dressing based on the pressure change, and further calculating a wound dressing fluid absorbent capacity based on the rate of pressure decay.

The method further includes communicating, by the therapy unit, the wound dressing fluid absorbent capacity to a remote electronic device.

In some embodiments, the method further includes comparing, by the processing circuit, the wound dressing fluid absorbent capacity at start up to a predetermined threshold condition including at least one of a minimum threshold or maximum threshold, and outputting an alert to the remote electronic device responsive to the wound dressing fluid absorbent capacity not satisfying the predetermined threshold condition.

In some embodiments, the method further includes calculating, by the processing circuit, an exudate volume in the wound dressing based on the wound dressing fluid absorbent capacity.

In some embodiments, the method further includes communicating, by the therapy unit, the exudate volume in the wound dressing to the remote electronic device at a predetermined time interval or responsive to a request.

In some embodiments, the method further includes calculating, by the processing circuit, a wound to dressing fluid absorbent rate based on the wound dressing fluid absorbent capacity.

In some embodiments, the method further includes communicating, by the therapy unit, the wound to dressing fluid absorbent rate to the remote electronic device at a predetermined time interval or responsive to a request.

In some embodiments, the method further includes opening, by the processing circuit, the sealable aperture at predetermined time intervals subsequent to start up or responsive to detecting a rapid pressure change.

In some embodiments, the method further includes calculating, by the processing circuit, an updated wound dressing fluid absorbent capacity each time the processing circuit opens the sealable aperture.

In some embodiments, the method further includes comparing, by the processing circuit, the updated wound dressing fluid absorbent capacity to a predetermined threshold condition including at least one of a minimum threshold or maximum threshold, and outputting an alert to the remote electronic device responsive to the wound dressing fluid absorbent capacity not satisfying the predetermined threshold condition.

In some embodiments, the method further includes calculating, by the processing circuit, an updated exudate volume in the wound dressing and/or an updated wound to dressing fluid absorbent rate based on the updated wound dressing fluid absorbent capacity.

Another implementation of the present disclosure is a non-transitory computer readable medium storing computer executable instructions which when executed by one or more processors cause the one or more processors to open a sealable aperture to induce a pressure change based on the pressure in a wound dressing to atmospheric pressure; receive a series of pressure data corresponding to the pressure change in the wound dressing based on at least one sensor, the at least one sensor coupled to the wound dressing; calculate a wound dressing fluid absorbent capacity corresponding to the pressure data; and output the wound dressing fluid absorbent capacity to a remote electronic device.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

BRIEF DESCRIPTION OF THE DRAWINGS

FIG. 4 is a block diagram of a control unit of the NPWT device of FIG. 1, according to an exemplary embodiment.

DETAILED DESCRIPTION

Overview

Referring generally to the FIGURES, a negative pressure wound therapy (NPWT) device, and components thereof are shown, according to various exemplary embodiments. In some embodiments, an NPWT system includes at least one sensor coupled to a wound dressing for a wound of a patient, a sealable aperture coupled to the at least one sensor, a processing circuit, and a communications circuit. The at least one sensor is configured to detect a pressure in the wound dressing. The processing circuit is configured to open a sealable aperture to induce a pressure change between the pressure in the wound dressing and atmospheric pressure, calculate a rate of pressure decay in the wound dressing corresponding to the pressure change, and calculate a wound dressing fluid absorbent capacity based on the rate of pressure decay. The communications circuit is coupled to the processing circuit and is configured to transmit data to a remote electronic device. This data can include the rate of pressure decay and/or the wound dressing fluid absorbent capacity.

In some embodiments, the NPWT system can open a sealable aperture to induce a change from negative pressure to atmospheric pressure in the wound dressing and calculate a rate of pressure decay based on the pressure change and the amount of exudate in the dressing. When compared to specified decay rates that correspond to known amounts of exudate in a wound dressing, the NPWT system can generate a value for the remaining wound dressing fluid absorbent capacity—the amount of exudate the dressing can still absorb from the wound. The wound dressing fluid absorbent capacity can provide useful information that can be utilized by care providers to determine if and when a wound dressing may need to be replaced. The wound dressing fluid absorbent capacity can further be used to calculate the exudate volume in the dressing and/or the wound to dressing fluid absorbance rate. These parameters can be useful in determining future changes to the care of a patient in response to the attributes of the wound to which the dressings are administered.

Negative Pressure Wound Therapy System

Figure 1:
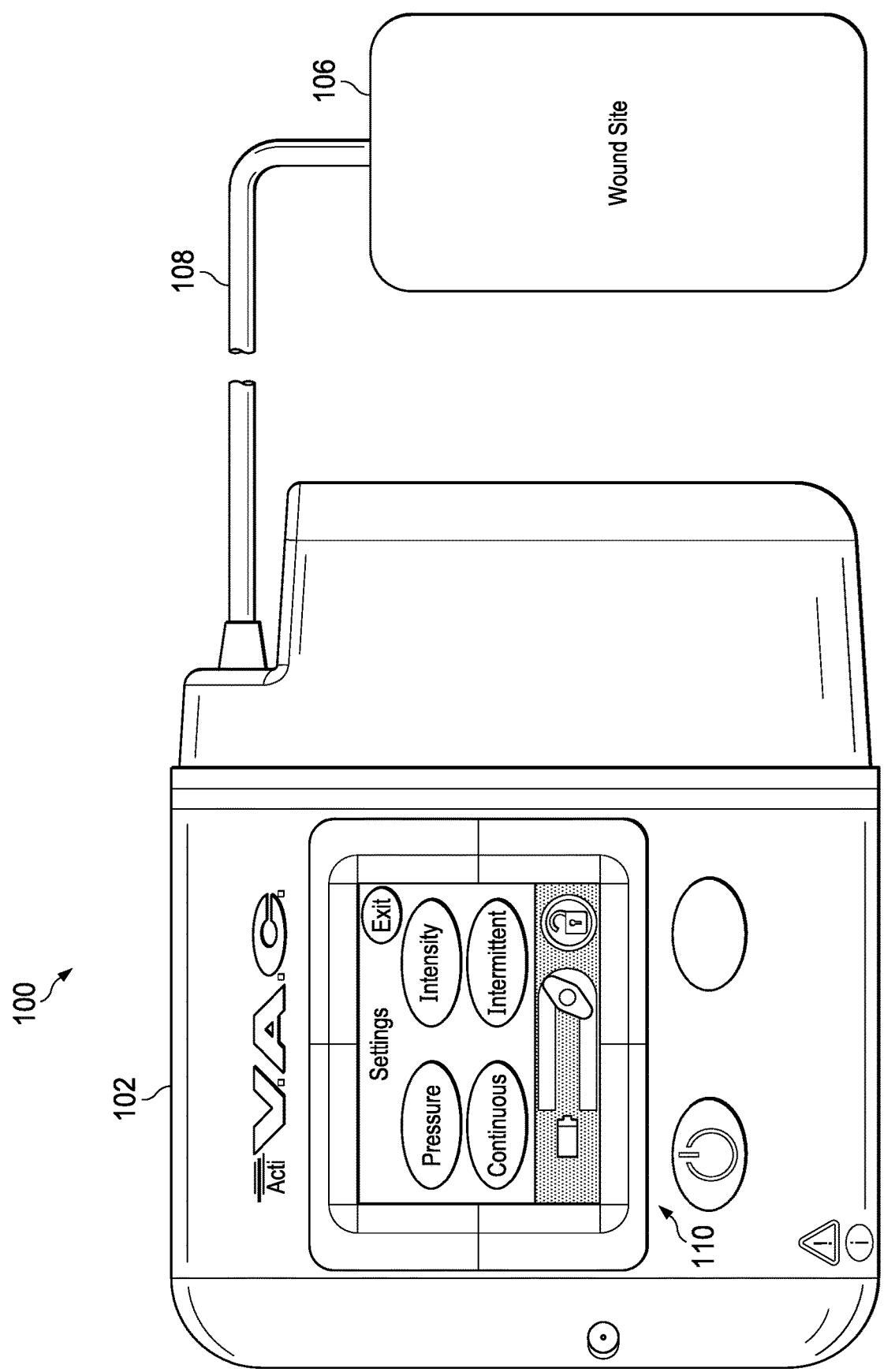
FIG. 1 is a drawing of a negative pressure wound therapy (NPWT) system including a NPWT device fluidly connected with a wound dressing at a wound site and a sensor system coupled to the wound dressing, according to an exemplary embodiment.
Figure 2:
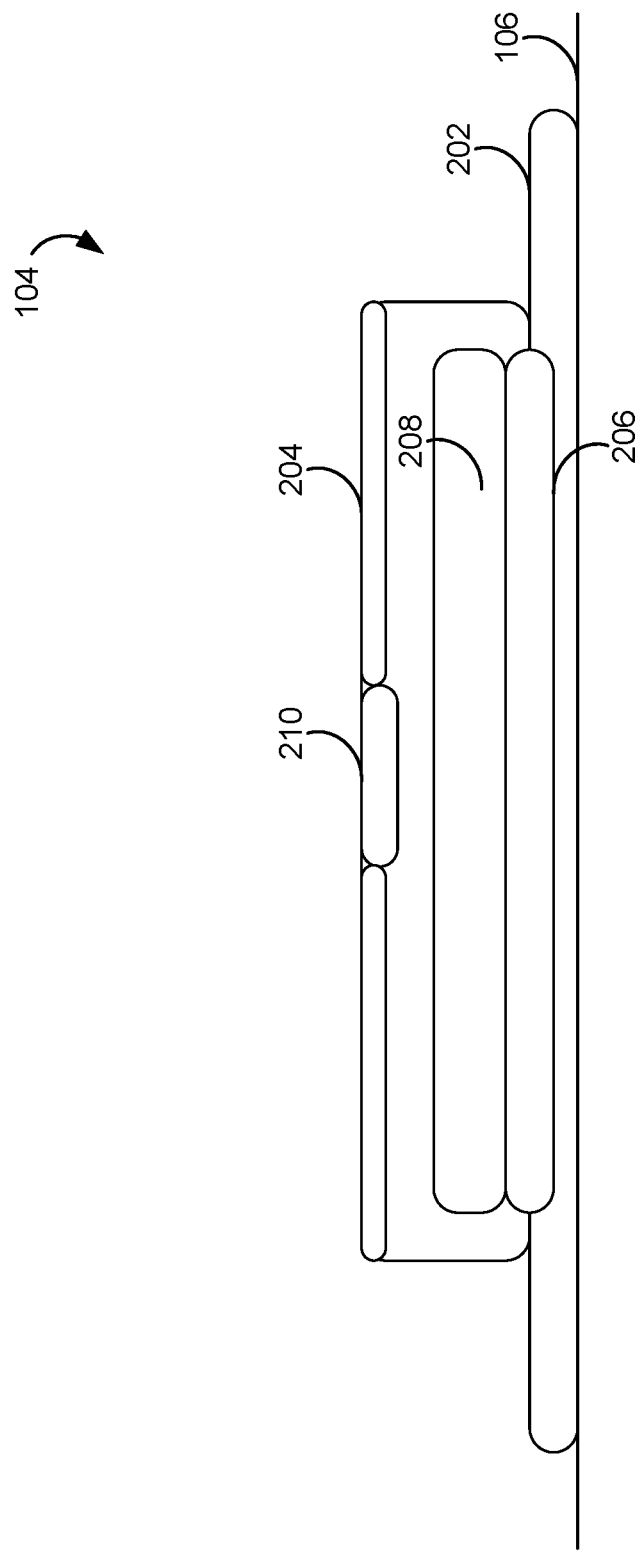
FIG. 2 is a schematic diagram illustrating a wound dressing of the NPWT system of FIG. 1, according to an exemplary embodiment.
Figure 3:
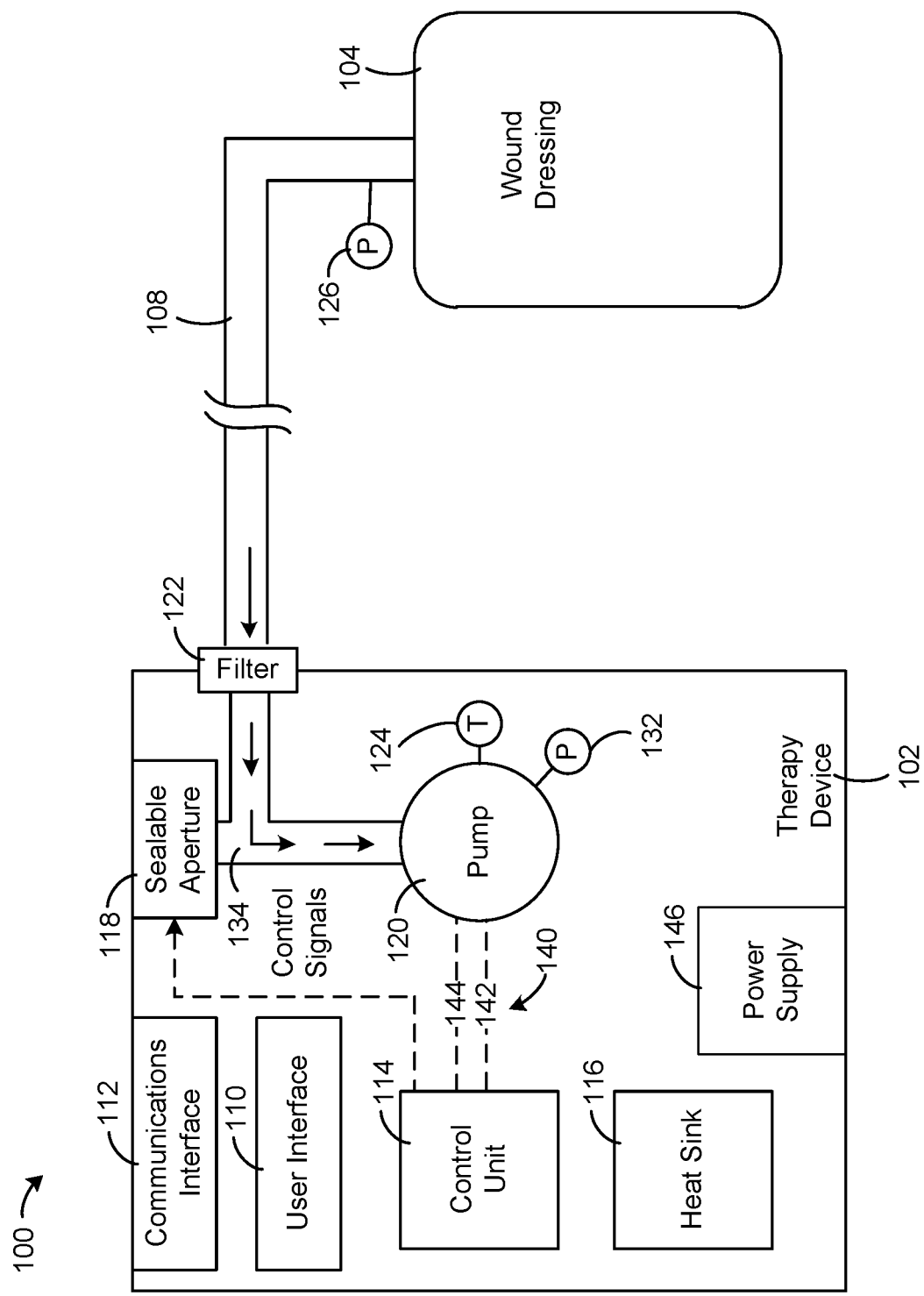
FIG. 3 is a block diagram illustrating the NPWT device and sensor system of FIG. 1 in greater detail, according to an exemplary embodiment.
Figure 5A:
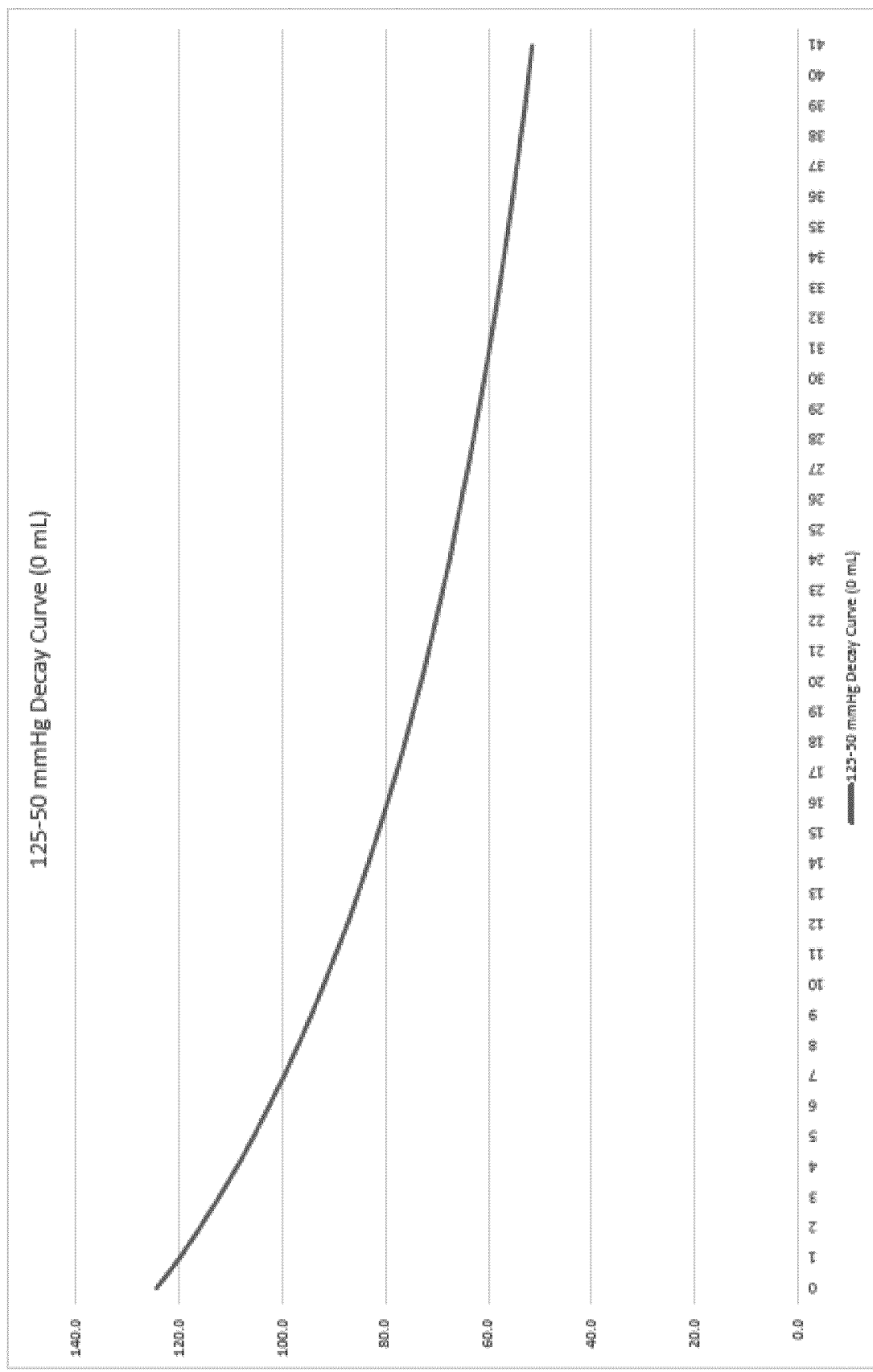
FIG. 5A is a decay curve illustrating a measured rate of pressure decay of a wound dressing containing 0 milliliters of exudate.
Figure 5B:
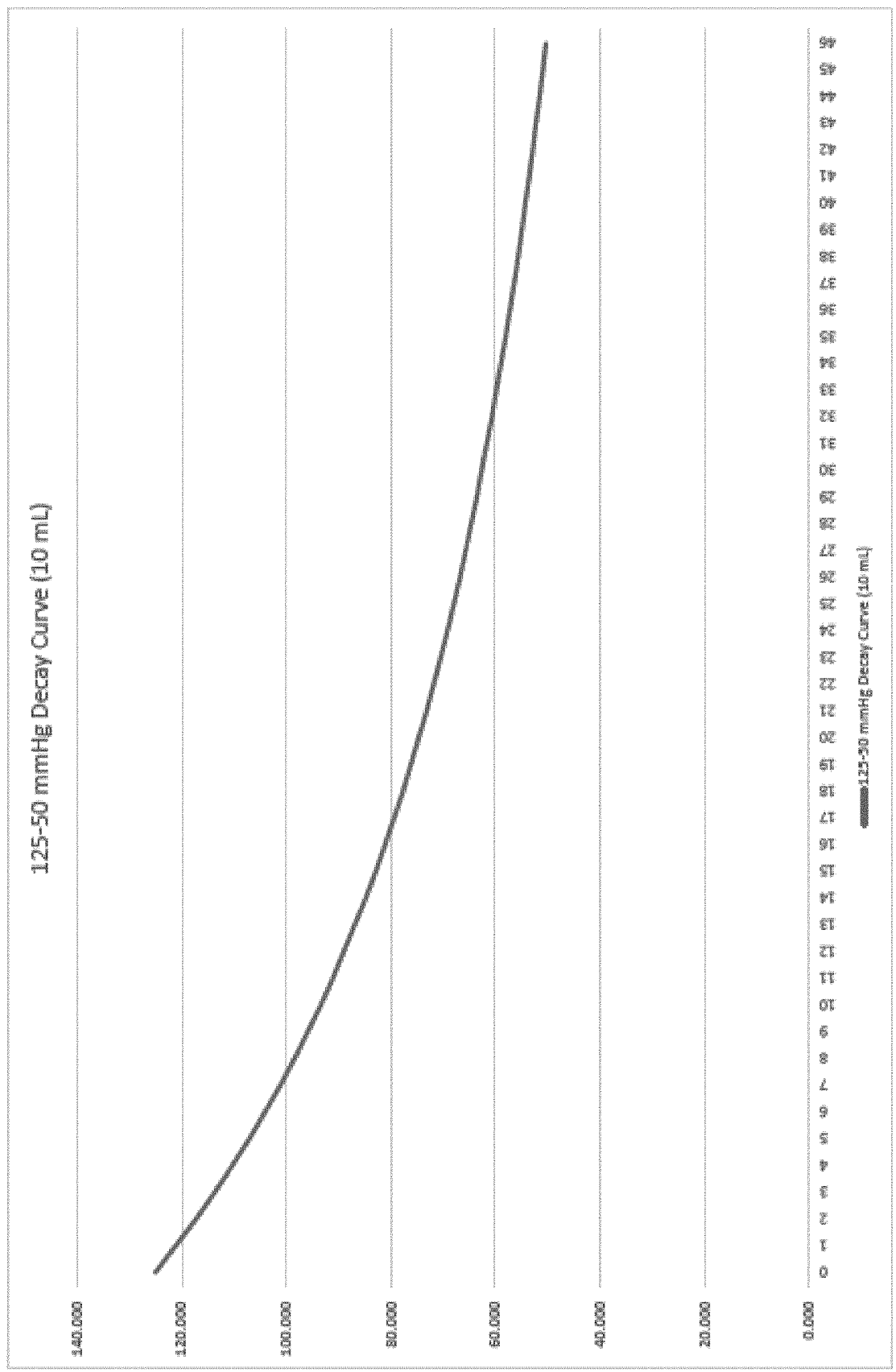
FIG. 5B is a decay curve illustrating a measured rate of pressure decay of a wound dressing containing 10 milliliters of exudate.
Figure 5C:
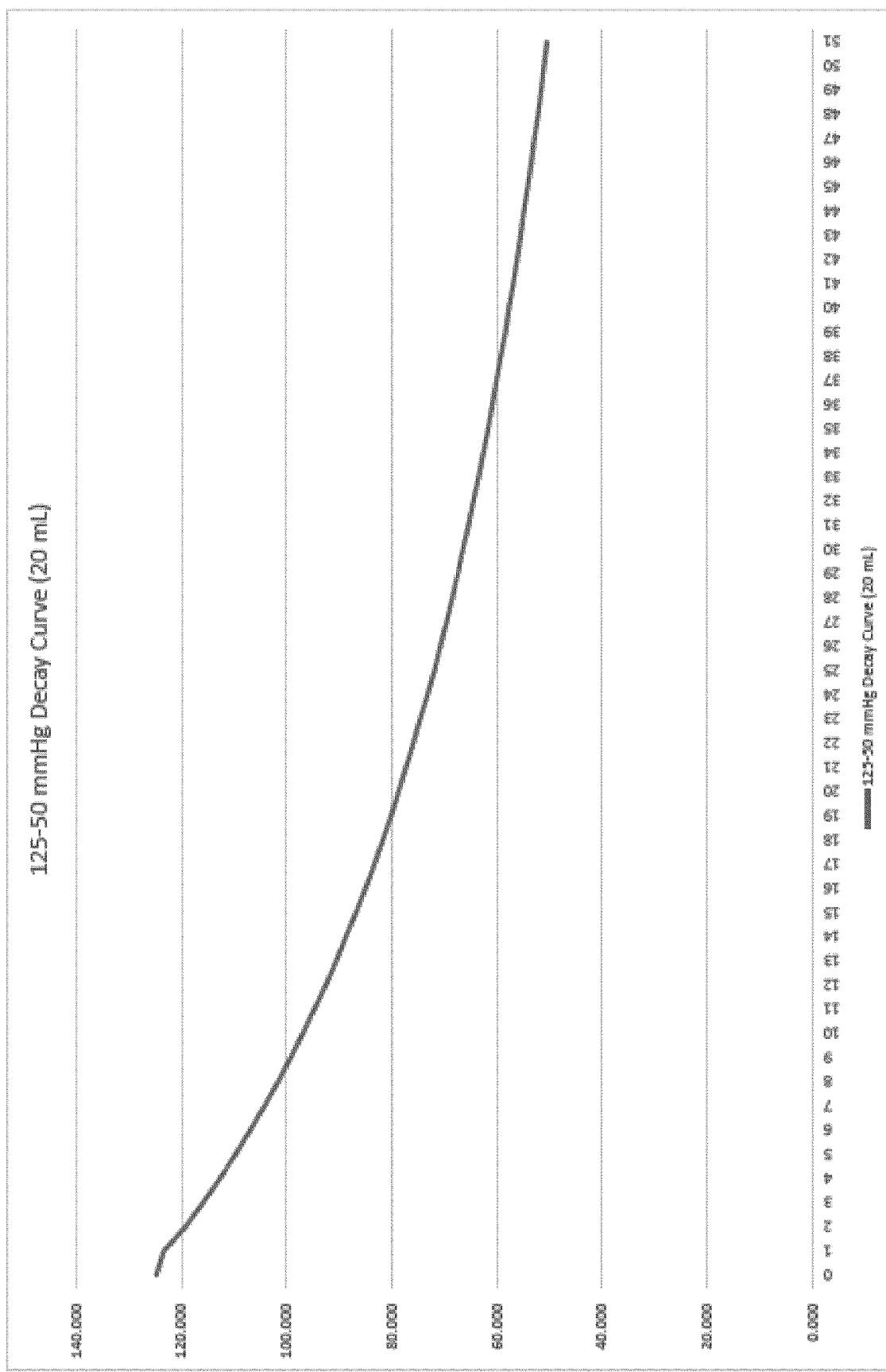
FIG. 5C is a decay curve illustrating a measured rate of pressure decay of a wound dressing containing 20 milliliters of exudate.
Figure 5D:
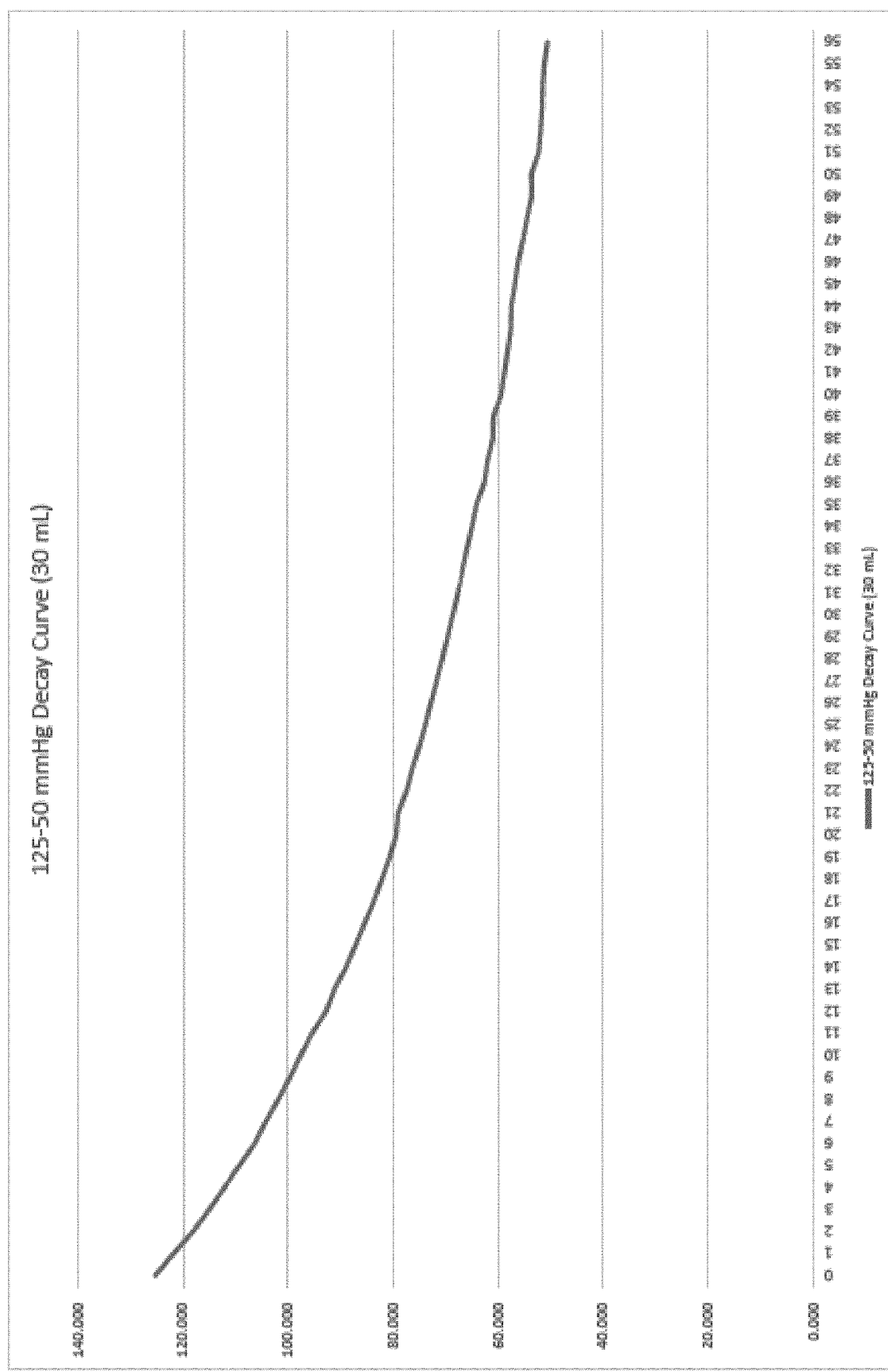
FIG. 5D is a decay curve illustrating a measured rate of pressure decay of a wound dressing containing 30 milliliters of exudate.
Figure 5E:
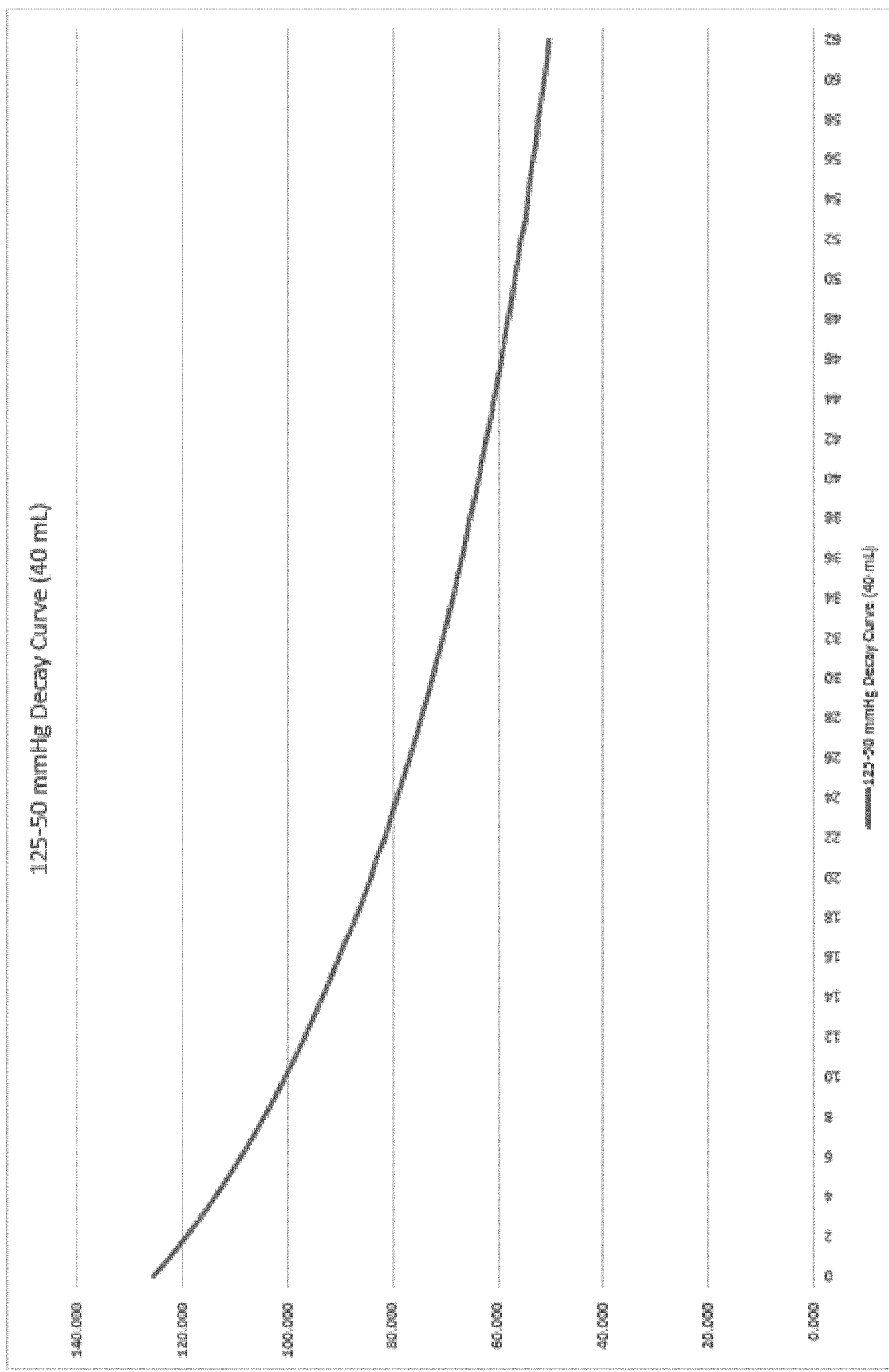
FIG. 5E is a decay curve illustrating a measured rate of pressure decay of a wound dressing containing 40 milliliters of exudate.

Referring now to FIGS. 1-3, a negative pressure wound therapy (NPWT) system 100 is shown, according to an exemplary embodiment. NPWT system 100 is shown to include a therapy device 102 (e.g., a therapy control and communication device) fluidly connected to a wound site 106 via tubing 108. Wound site 106 may include a tissue wound as well as a wound dressing that covers the tissue wound and adheres to a patient's skin. Several examples of wound dressings which can be used in combination with NPWT system 100 are described in detail in U.S. Pat. No. 7,651,484 granted Jan. 26, 2010, U.S. Pat. No. 8,394,081 granted Mar. 12, 2013, and U.S. patent application Ser. No. 14/087,418 filed Nov. 22, 2013. The entire disclosure of each of these patents and patent applications is incorporated by reference herein.

Therapy device 102 can be configured to provide negative pressure wound therapy by reducing the pressure at wound site 106. Therapy device 102 can draw a vacuum at wound site 106 (relative to atmospheric pressure) by removing wound exudate, air, and other fluids from wound site 106. Wound exudate may include fluid that filters from a patient's circulatory system into lesions or areas of inflammation. For example, wound exudate may include water and dissolved solutes such as blood, plasma proteins, white blood cells, platelets, and red blood cells. Other fluids removed from wound site 106 may include instillation fluid previously delivered to wound site 106. Instillation fluid can include, for example, a cleansing fluid, a prescribed fluid, a medicated fluid, an antibiotic fluid, or any other type of fluid which can be delivered to wound site 106 during wound treatment.

In some embodiments, therapy device 102 may include a canister (not shown). The fluids removed from wound site 106 pass through tubing 108 and are collected in the canister, in some embodiments. The canister may collect wound exudate and other fluids removed from wound site 106. Reduced pressure within the canister can be translated to wound site 106 via tubing 108 such that wound site 106 is maintained at the same pressure as the canister.

Referring now to FIG. 2, a schematic diagram illustrating wound dressing 104 in greater detail is shown, according to an exemplary embodiment. In some embodiments, wound dressing 104 is configured to extend a first length along the first direction, and a second length greater than the first length along the second direction. It will be appreciated that when wound dressing 104 is applied to a wound (which will typically extend primarily in a single wound direction) at wound site 106, wound dressing 104 may generally be aligned with the wound such that the second direction is aligned with the single wound direction. Wound dressing 104 can be an incisional wound dressing for placement over a closed incision.

Wound dressing 104 can include a first layer 202. First layer 202 can be a patient interface layer on a lower side of wound dressing 104. In some embodiments, first layer 202 includes at least one of perforated silicone or a polyurethane gel adhesive. In some embodiments, first layer 202 includes an adhesive, such as an acrylic adhesive. In various such embodiments, first layer 202 enables wound dressing 104 to be applied with a pneumatic seal to wound site 106, while being able to be repositioned and to still maintain an effective seal of wound site 106.

Wound dressing 104 can include a second layer 204. Second layer 204 can be a dressing cover. Second layer 204 be made from a polyurethane film, and can be coated with an acrylic adhesive.

Wound dressing 104 can include a third layer 206. Third layer 206 allow transport of negative pressure from tubing 108 to the incision site, and transport of wound fluids into wound dressing 104. Third layer 206 can include at least one of manifolding material, wicking material, or bolstering material. For example, third layer 206 can include at least one of a foam material (e.g., compressed polyolefin material manufactured by ESSENTRA) or a non-woven material (e.g., co-polyester material manufactured by LIBELTEX).

In some embodiments, wound dressing 104 includes a fourth layer 208. Fourth layer 208 can include an absorbent core (e.g., TEXSUS 500 gsm superabsorbent material textile; GELOK 300 GSM superabsorbent material textile). Fourth layer 208 can receive and store fluids to be stored for the duration of therapy. Fourth layer 208 can include a perforated film layer disposed between fourth layer 208 and third layer 206 to prevent backflow of liquid from fourth layer 208 into third layer 206. In some embodiments, the fourth layer 208 forms at least a threshold fraction of the volume of wound dressing 104, such that at least the threshold fraction by volume of wound dressing 104 includes a super absorbent material. The threshold fraction may be twenty percent. The threshold fraction may be thirty percent. The threshold fraction may be fifty percent.

In some embodiments, wound dressing 104 includes an aperture 204. Wound dressing can be coupled to a negative pressure source, such as therapy unit 102 via aperture 204 (and tubing 108) so that the negative pressure applied from therapy device 102 via tubing 108 is applied to wound dressing 104 (and thus the wound). In some embodiments, negative pressure interface 202 is a pad. Aperture 204 can include a liquid blocking filter. Aperture 204 can supplement or replace filter 122. Aperture 204 can allow the transmission of negative pressure or topical oxygen via tubing 108 from the wound dressing 104, but prevent the egress of wound fluids. Aperture 204 may also provide a viral and bacterial filter for wound site 106. In some embodiments, wound dressing 104 is configured to collapse (e.g., reduce in volume) while negative pressure is applied to wound dressing 104 by pump 120.

Referring particularly to FIG. 3, a block diagram illustrating therapy device 102 in greater detail is shown, according to an exemplary embodiment. Therapy device 102 is shown to include a pump 120, a filter 122, a valve 118, a heat sink 116, and a control unit 114. Pump 120 is intended to create a reduced pressure (e.g., to be applied to wound dressing 104). Although pump 120 is intended for use with wound dressing that do not include a canister (e.g., canister-free dressing systems), in some embodiments, pump 120 can be fluidly coupled to canister (e.g., via conduit 134) and can be configured to draw a vacuum within the canister by pumping air out of the canister. Pump 120 can be controlled by control unit 114, as described in greater detail below.

Pump 120 is a piezoelectric pump, in some embodiments. In some embodiments, the pump 120 includes a movable member (e.g., diaphragm) which undergoes mechanical displacement based on a voltage applied to the movable member, such as by oscillating in response to receiving an alternating current. By oscillating, the movable member can push air to generate the negative pressure applied by the pump 120. The movable member can be metallic. Pump 120 can include a copper disc with a slit which opens when pushed by the movable member. In some embodiments, the movable member oscillates at approximately 21 kHz. Under typical operational conditions, the pump 120 can operate silently or near silently (e.g., from a human audible perspective). For example, noise generated by pump 120 can be less than a noise threshold which can be heard by a typical user. The noise threshold may be less than or equal to 30 dBa. The noise threshold may be less than or equal to 15 dBa. The noise threshold may be zero dBa. In an embodiment, pump 120 is a Vacuum Pump manufactured by Koge Micro Tech Co., Ltd. Pump 120 can include a piezo-acoustic pump. Pump 120 can include a diaphragm pump, in other embodiments.

In some embodiments, NPWT system 100 includes a plurality of pumps 120. For example, therapy device 102 may include multiple pumps 120, each coupled to tubing 108 and controlled by control unit 114. NPWT system 100 may include a plurality of therapy devices 102, each of which may include one or more pumps 120.

Filter 122 can be positioned between tubing 108 and pump 120 (e.g., along conduit 134). Filter 122 can be configured to prevent liquid or solid particles from entering conduit 134 and reaching pump 120. Filter 122 may include, for example, a bacterial filter that is hydrophobic and/or lipophilic such that aqueous and/or oily liquids will bead on the surface of filter 122. Pump 120 can be configured to provide sufficient airflow through filter 122 that the pressure drop across filter 122 is not substantial (e.g., such that the pressure drop will not substantially interfere with the application of negative pressure to wound site 106 from therapy device 102).

Sealable aperture 118 can be fluidly connected with pump 120 and filter 122 via conduit 134. In some embodiments, valve 118 is configured to control airflow between conduit 134 and the environment around therapy device 102. For example, sealable aperture 118 can be opened to allow airflow between conduit 134 and the environment around therapy device 102, and closed to prevent airflow between conduit 134 and the environment around therapy device 102. Sealable aperture 118 can be opened and closed by control unit 114, described in greater detail below. When sealable aperture 118 is closed, pump 120 can draw a vacuum within conduit 134 by causing airflow through filter 122 in a first direction, as shown in FIG. 2. When sealable aperture 118 is open, airflow from the environment around therapy device 102 may enter conduit 134 and fill the vacuum within conduit 134 to return the wound dressing to atmospheric pressure. NPWT system 100 may include a plurality of sealable apertures 118. While FIG. 3 depicts sealable aperture 118 as a two-way exhaust valve coupled to pump 120 via conduit 134, the sealable aperture may also be an internal aperture in pump 120 (or wound dressing 104) by which pump 120 (or wound dressing 104) may inherently leak during typical operation. As shown in FIG. 3, the pump 120 may be directly coupled to the wound dressing 104 via the tubing 108.

Heat sink 116 may be provided to increase a rate of heat dissipation from therapy device 102 or components thereof, such as pump 120. For example, heat sink 116 can be configured to have a relatively greater coefficient for convective heat transfer than other components of therapy device 102, such as by having a relatively greater surface area to volume ratio. Heat sink 116 may be mounted to control unit 114, pump 120, or a circuit board (not shown) to which control unit 114 and/or pump 120 are mounted. In some embodiments, heat sink 116 includes a plurality of fins.

Control unit 114 can be configured to operate pump 120, valve 118, and/or other controllable components of therapy device 102. In some embodiments, control unit 114 is configured to operate pump 120 by transmitting a control signal to pump 120 via alternating current circuit 140, which includes first arm 142 and second arm 144. The arms 142, 144 may be associated with corresponding pump drive electrodes for pump 120.

In some embodiments, therapy device 102 includes a variety of sensors, which can communicate sensor measurements to control unit 114. For example, therapy device 102 is shown to include a temperature sensor 124 configured to measure a temperature of pump 120 and communicate the measured temperature of pump 120 to control unit 114. Temperature sensor 124 may be a thermocouple.

In some embodiments, NPWT system 100 includes a pressure sensor 126 configured to measure at least one of (1) the pressure at wound site 106 or (2) the pressure at the pump 120, and communicate the measured pressure to control unit 114. The pressure at the wound site 106 and pressure at the pump 120 may be essentially the same as there may be little to no fluid in the tubing between the wound dressing and the pump, eliminating a potential pressure difference between the two points. Control unit 114 can use the sensor measurements as inputs to various control operations performed by control unit 114, including adjusting operation of pump 120 based on sensor measurements or opening the sealable aperture in the event a large pressure change is detected. Pressure sensor 126 may be included in therapy device 102, or may be a wireless pressure sensor module remote from therapy device 102 and included in wound dressing 104.

In some embodiments, therapy device 102 includes a user interface 110. User interface 110 may include one or more buttons, dials, sliders, keys, or other input devices configured to receive input from a user. User interface 110 may also include one or more display devices (e.g., LEDs, LCD displays, etc.), speakers, tactile feedback devices, or other output devices configured to provide information to a user. In some embodiments, the pressure measurements recorded by pressure sensors 126 are presented to a user via user interface 110. User interface 110 can also display alerts generated by control unit 114.

In some embodiments, therapy device 102 includes a data communications interface 112 (e.g., a USB port, a wireless transceiver, etc.) configured to receive and transmit data. Communications interface 112 may include wired or wireless communications interfaces (e.g., jacks, antennas, transmitters, receivers, transceivers, wire terminals, etc.) for conducting data communications external systems or devices. In various embodiments, the communications may be direct (e.g., local wired or wireless communications) or via a communications network (e.g., a WAN, the Internet, a cellular network, etc.). For example, communications interface 112 can include a USB port or an Ethernet card and port for sending and receiving data via an Ethernet-based communications link or network. In another example, communications interface 112 can include a Wi-Fi transceiver for communicating via a wireless communications network or cellular or mobile phone communications transceivers.

In some embodiments, therapy device 102 includes a power supply 146, which can provide power for operation of pump 120, control unit 114, and other components of therapy device 102.

In some embodiments, such as if pump 120 is a mechanical pump, therapy device 102 includes a coin cell power supply, and pressure sensor 126 can include a wireless pressure sensor module, as discussed above, that can receive power from the coin cell power supply and communicates therapy parameters via at least one of illumination of a display (e.g., an LED display) or wirelessly transmitting a dressing capacity notification to a remote electronic device, such as a smartphone. In various such embodiments in which pump 120 is a mechanical pump, sealable aperture 118 may include a relief or isolation valve included in wound dressing 104.

Negative Pressure Wound Therapy Systems for Determining Wound Dressing Fluid Absorbent Capacity Referring now to FIG. 4, a block diagram illustrating control unit 114 in greater detail is shown, according to an exemplary embodiment. Control unit 114 can be used with various wound dressings and sensors described herein. Control unit 114 can include an internal closed-loop control board, with a microprocessor and pressure sensor 126. As noted above, as there is no fluid in tubing 108 between wound dressing 104 and pressure sensor 126, pressure detected by pressure sensor 126 may be equal or substantially equal to pressure of wound dressing 104.

Control unit 114 is shown to include a processing circuit 146 including a processor 148 and memory 150. Processor 148 may be a general purpose or specific purpose processor, an application specific integrated circuit (ASIC), one or more field programmable gate arrays (FPGAs), a group of processing components, or other suitable processing components. Processor 148 is configured to execute computer code or instructions stored in memory 150 or received from other computer readable media (e.g., CDROM, network storage, a remote server, etc.).

Memory 150 may include one or more devices (e.g., memory units, memory devices, storage devices, etc.) for storing data and/or computer code for completing and/or facilitating the various processes described in the present disclosure. Memory 150 may include random access memory (RAM), read-only memory (ROM), hard drive storage, temporary storage, non-volatile memory, flash memory, optical memory, or any other suitable memory for storing software objects and/or computer instructions. Memory 150 may include database components, object code components, script components, or any other type of information structure for supporting the various activities and information structures described in the present disclosure. Memory 150 may be communicably connected to processor 148 via processing circuit 146 and may include computer code for executing (e.g., by processor 148) one or more processes described herein. When processor 148 executes instructions stored in memory 150, processor 148 generally configures control unit 114 (and more particularly processing circuit 146) to complete such activities. It will be appreciated that some or all the functions executed by control unit 114 may be executed by a remote computing device, such as a device for use by a clinician that is communicatively coupled to therapy device 102.

Control unit 114 is shown to include a pump controller 152. Pump controller 152 generates control signals to control operation of pump 120. Pump controller 152 can configure parameters of the control signals, such as current, voltage, frequency, amplitude, or intermittency. In some embodiments, pump controller 152 generates alternating current control signals having a root mean square (RMS) voltage, and transmits the control signals to pump 120 via alternating current circuit 140. For example, pump controller 152 can generate the control signals to have a particular RMS voltage by modulating a first phase angle of a first signal component associated with first arm 142 relative to a second phase angle of a second signal component associated with second arm 144.

Control unit 114 is shown to include a therapy parameter calculator 154. Therapy parameter calculator 154 can receive sensor measurements from various sensors coupled to therapy device 102, such as pressure sensors 132, 126.

Each of sensors 124, 126, 132 may output a sensor measurement in a sensor-specific unit of measure, such as capacitance or a voltage representative of capacitance; therapy parameter calculator 154 can be configured to convert the received sensor measurement to temperature or pressure as appropriate. For example, therapy parameter calculator 154 can store calibration functions that when executed, convert sensor measurements from sensors 124, 126, 132 to appropriate units of measure.

Therapy parameter calculator 154 can calculate one or more therapy parameters based on received sensors measurements. For example, therapy parameter calculator 154 can receive a pressure measurement of pressure sensor 126 (or similarly a pressure measurement from pressure sensor 132), and determine the rate of pressure decay based on the pressure measurement. When the sealable aperture is opened and sub-atmospheric pressure in the wound dressing rises, therapy parameter calculator 154 can calculate the rate of pressure decay to be a rate of change of pressure as a function of time at a start time of when the sealable aperture is opened to an end time of when the pressure in wound dressing 104 is equal to atmospheric pressure.

Therapy parameter calculator 154 can calculate a fluid absorbent capacity of the wound dressing based on the rate of pressure decay. The wound dressing fluid absorbent capacity can represent an amount of fluid wound dressing 104 can absorb, taking into account any exudate that may already be absorbed by wound dressing 104. Therapy parameter calculator 154 can calculate a value of the wound dressing fluid absorbent capacity by correlating the calculated rate of pressure decay to calibration curves of known rates of pressure decay for specified fluid volumes that can be stored in memory 150, as described below with respect to FIGS. 4A-4E.

Therapy parameter calculator 154 can calculate an exudate volume in the wound dressing based on the wound dressing fluid absorbent capacity. The exudate volume can represent an amount of exudate already absorbed by the wound dressing 104. Therapy parameter calculator 154 can calculate the exudate volume in the wound dressing based on a maximum capacity of the wound dressing and the wound dressing fluid absorbance capacity (the amount of fluid the dressing can still absorb). The maximum capacity of wound dressing 104 can be specific to the type of wound dressing used and may be stored in memory 150.

Therapy parameter calculator 154 can calculate a wound to dressing fluid absorbance rate based on the wound dressing fluid absorbent capacity. Memory 150 can store one or more previous values for the wound dressing fluid absorbent capacity, as well as the time at which the previous value(s) recorded. When the wound dressing fluid absorbent capacity is updated by therapy parameter calculator 154, the updated wound dressing fluid absorbent capacity and a time at which it was calculated can be stored by memory 150. Therapy parameter calculator 154 can compare the updated and previous values for the wound dressing fluid absorbent capacity, determine an amount of exudate produced by the wound and subsequently absorbed during the time period, and calculate the wound to dressing fluid absorbance rate.

Pump controller 152 can control operation of pump 120 based on the sensor inputs from pressure sensors 126, 132. For example, the pressure sensors 126, 132 can detect a rapid change in pressure in the wound dressing 104, such as the case of a fluid bolus entering the dressing. Pump controller 154 can detect a rapid change by comparing the rate of change between two pressure measurements and comparing the rate of change to one of a minimum or a maximum threshold, at which point the control unit 114 can communicate with pump controller 152 to adjust pump 120 to maintain a set negative pressure on the wound site 106 or send a command to open the sealable aperture to obtain an update wound dressing fluid absorbent capacity. Control unit 114 can use closed-loop pressure feedback that can be used to directly control the effectiveness of negative pressure wound therapy based on pressure on the wound, adjusting the pump 120 as necessary. In some embodiments, pump controller 152 receives a control command from a remote source and controls operation of pump 120 based on the received control command.

Alert generator 156 can generate alerts based on the calculated therapy parameter(s): wound dressing fluid absorbent capacity, exudate volume in the wound dressing, or wound to dressing fluid absorbance rate. Alert generator 156 can compare the therapy parameter(s) to a predetermined threshold condition, including at least one of a minimum threshold or a maximum threshold, and output an alert responsive to the therapy parameter not satisfying the predetermined threshold condition. Alert generator 156 can store the alert. The predetermined threshold condition may be associated with therapy parameter(s) including but not limited to malfunctions (results of out of the norm calculations), minimum capacity, maximum capacity, and wound dressing fluid levels.

Alert generator 156 can cause data communications interface 112 to transmit the alert to a remote destination. Alert generator 156 can also be used to transmit sensor measurements to the remote destination, to enable remote monitoring of therapy status. For example, alert generator 156 can generate alerts indicative of sensor measurements which can be used to determine when a dressing may need to be changed, whether a dressing is defective, or how much fluid a wound may produce. In addition, alert generator 156 can generate alerts of patient ambulatory activity. Alert generator 156 can be used to transmit alerts and/or sensor measurement in response to a remote request from therapy unit 102 (e.g., via user interface 110) or a remote electronic device (e.g., a device operated by a clinician that is communicatively coupled to control unit 114).

Alert generator 156 can generate an alert indicative of end of dressing life. For example, alert generator 156 can calculate the wound dressing absorbent capacity based on the rate of pressure decay, and determine the corresponding capacity of the dressing. Should the wound dressing absorbent capacity be less than or equal to a minimum threshold (similarly, should the exudate volume in the wound dressing be greater than or equal to a maximum threshold of the wound dressing) alert generator 156 can output the alert indicative of end of wound dressing life using the user interface 110 and/or transmit the alert to a remote destination, such as a remote electronic device operated by caregiver in order to inform the caregiver of the necessary replacement of the wound dressing.

In some embodiments, alert generator 156 can generate an estimated lifetime of a wound dressing based on the historical therapy data of the particular patient, taking into account factors such as type of wound, rate of exudate production, and healing stage of the wound. An estimated lifetime of the dressing can be modeled by the therapy parameter calculator 154 based on parameters such as the dimensions of the wound, the expected or calculated wound to dressing fluid absorbent rate, and amount of exudate volume already absorbed that can be stored in memory 150. Therapy parameter calculator 154 can model the lifetime of the wound dressing according to the progression of therapy and historical data stored in memory 150 such that the model can become more accurate as therapy progresses.

Referring generally to FIGS. 5A-E, five graphs illustrating exemplary rate of pressure decay curves at varying exudate volumes (0 mL-40 mL) are shown. These rate of pressure decay curves were obtained during testing via measuring a known induced change in pressure from 125 mmHg to 50 mmHg of a wound dressing containing a known exudate volume. The rate of pressure decay was recorded for a new wound dressing containing 0 mL of exudate in FIG. 4A, and at increasing intervals of 10 mL with a maximum of 40 mL, FIGS. 4B-4E, respectively. These curves track the decay in sub-atmospheric pressure to atmospheric pressure starting at the point in time at which the processing circuit opens the sealable aperture (e.g., the two-way exhaust valve or the pump with an internal leak) to decrease the difference in pressure. These curves can be used to generate, via therapy parameter calculator 154, a calibration function that takes in a rate of pressure decay and can produce a corresponding wound dressing fluid absorbent capacity. The wound dressing used for rate of pressure decay testing may be a dressing of the NANOVA™ Therapy System manufactured by ACELITY L.P., Inc. of San Antonio, Tex., and may have a size of approximately 13 cm by 13 cm.

Upon calculation of a rate of pressure decay, the processor 148 can retrieve the calibration function and the calculated rate of pressure decay from memory 150 and pass them to therapy parameter calculator 154. Therapy parameter calculator 154 can generate a wound dressing fluid absorbent capacity by using the rate of decay of pressure as an input to the calibration function. The output of the calibration function may be the wound dressing fluid absorbent capacity or it can be a fluid level (i.e., exudate volume) in the dressing that therapy parameter calculator 154 can use to calculate a corresponding wound dressing fluid absorbent capacity.

During therapy, at predetermined time intervals or when a large pressure change is detected, such as the case of a fluid bolus entering the dressing, the control unit 114 and processing circuit 146 can open the sealable aperture to return the wound dressing to atmospheric pressure. The processor 148 can receive and analyze data from the pressure sensor(s) coupled to the wound dressing over a time period beginning at the time the control unit 114 and processing circuit 146 opens the sealable aperture and ending at a time at which the pressure in the wound dressing is equal to the atmospheric pressure (50 mmHg). The processor 148 can send the data to the therapy parameter calculator 154, where the new calculated rate of decay can be compared to the calibration curves (and thus the corresponding known fluid levels) stored in memory 150 to determine the fluid level in the dressing at the time the rate of decay was recorded.

Figure 6:
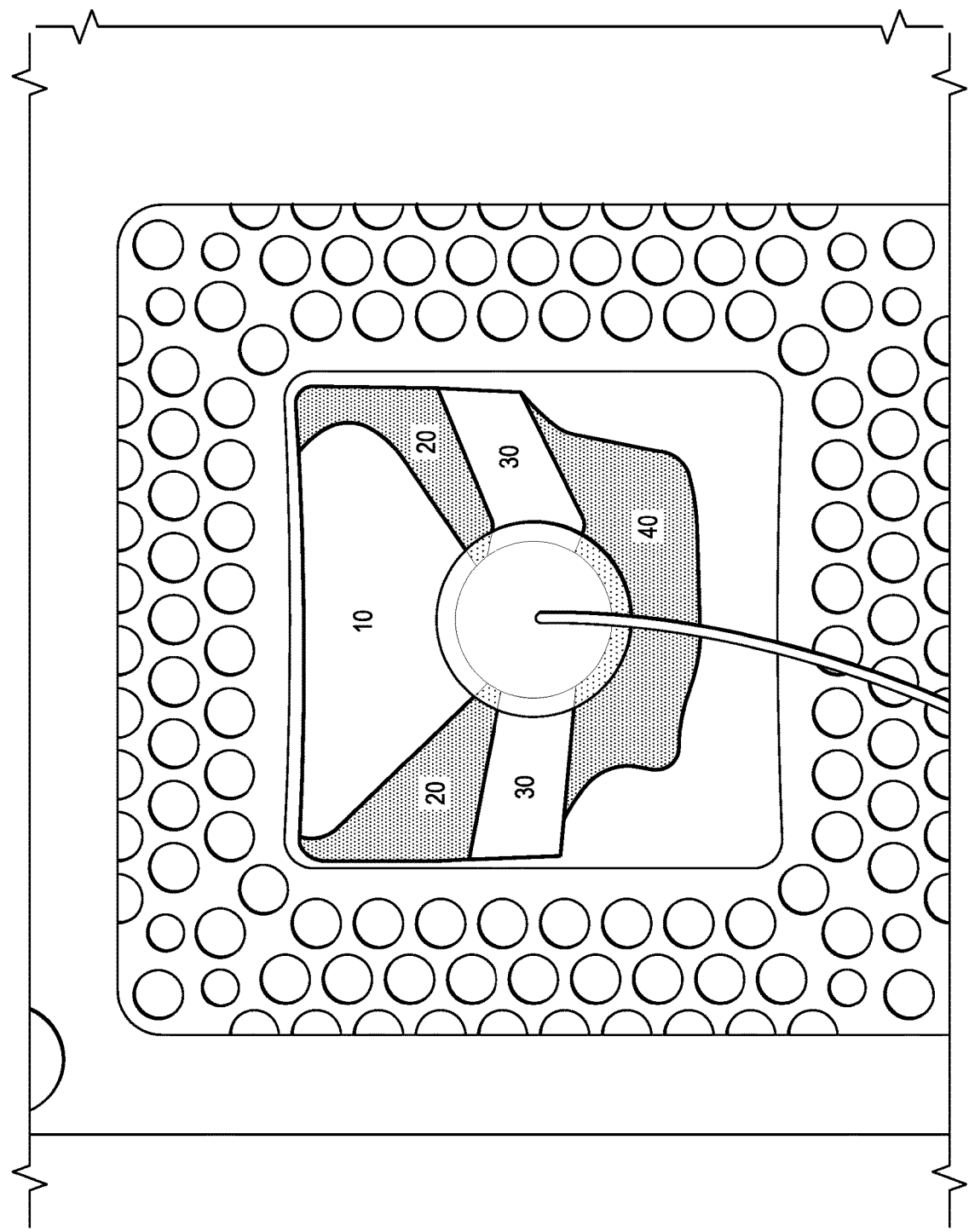
FIG. 6 is an example embodiment of a wound dressing post-testing illustrating the apparent capacity of the wound dressing at varying exudate volumes.

In some embodiments, the wound dressing may fill evenly with fluid as illustrated by FIG. 6. The wound dressing can fill evenly with exudate fluid to evenly disperse pressure exerted by the fluid across the wound dressing so as to eliminate excess pressure on areas of the wound that may excrete high volumes of exudate.

Control Processes

Figure 7:
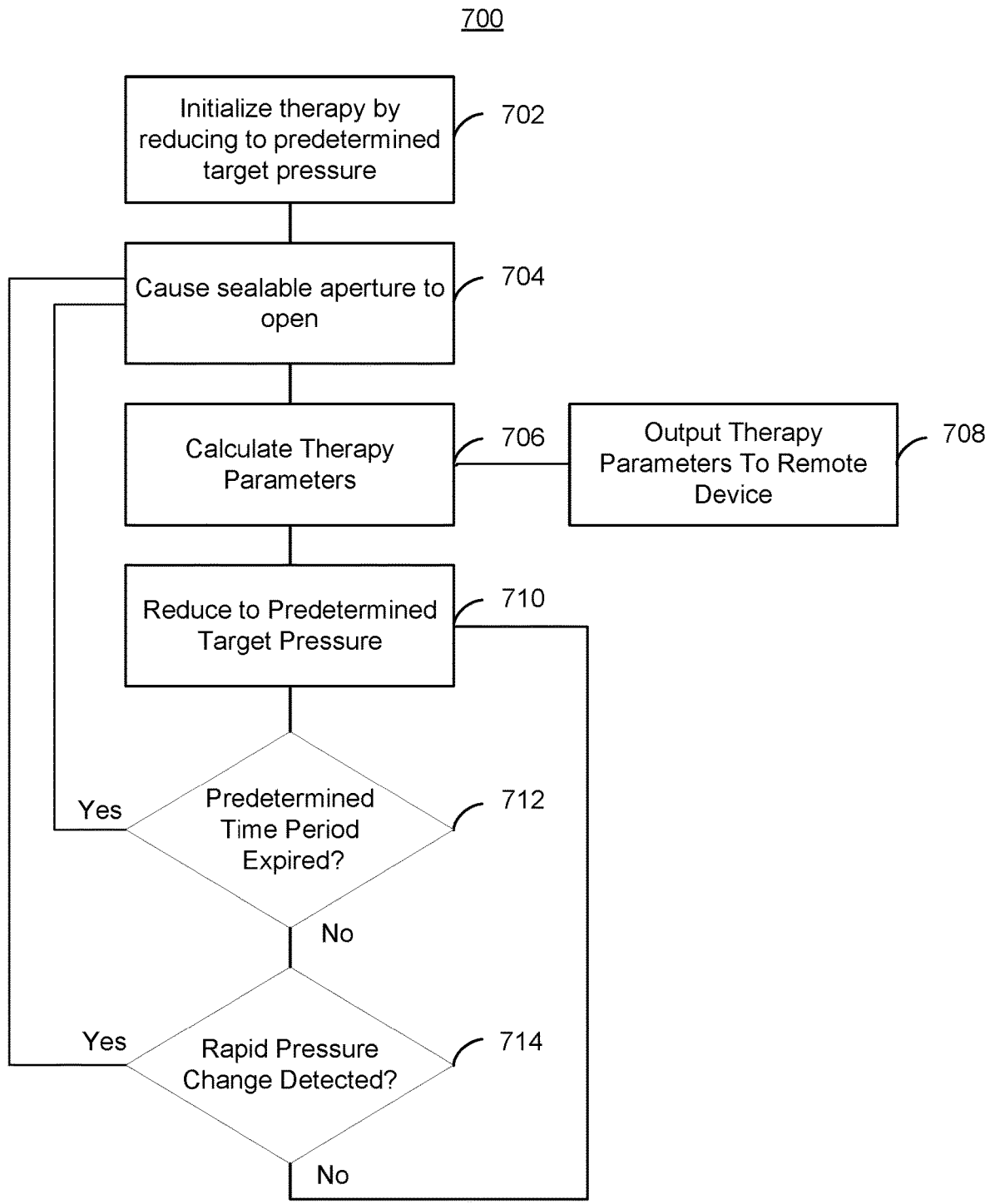
FIG. 7 is a flowchart of a process for operating the NPWT device of FIG. 1, according to an exemplary embodiment.

Referring now to FIG. 7, a flowchart of a process 700 for operating a sensor system associated with a negative pressure wound therapy (NPWT) device is shown, according to an exemplary embodiment. Process 700 can be performed by the NPWT system 100, as described with reference to FIGS. 1-4. For example, process 700 can be performed by sensors 126 and/or 132, and therapy device 102 using control unit 114 to control pump 120 based on sensor measurements received from sensors 126 and/or 132.

In some embodiments, pump controller 152 controls operation of pump 120 to draw down pressure in the wound dressing 104 to a predetermined target pressure (step 702). The predetermined target pressure may be approximately 125 mmHg. Pump controller 152 receives pressure data from a pressure sensor measuring the pressure of wound dressing 104. The sensor can be coupled to control unit 114, and may be removably attached to the wound dressing or mounted in the therapy unit. Pump controller 152 executes closed loop control to adjust pump 120 to maintain target reduced pressure at substantially all times throughout therapy.

Subsequent to causing draw down to the predetermined target pressure, control unit 114 can cause sealable aperture 118 to open to allow pressure in wound dressing 104 to equalize with outside pressure (e.g., atmospheric pressure) (step 704). Control unit 114 can open sealable aperture 188 at the start of therapy to calculate of a set of initial therapy parameters.

Therapy parameter calculator 154 can calculate the rate of pressure decay, and in turn an initial (e.g., starting) fluid absorbent capacity of wound dressing 104, based on pressure data regarding wound dressing 104 received from pressure sensor(s) 126, 132, based on the change in pressure that occurs when control unit 114 causes sealable aperture 118 to open (step 706). Control unit 114 can store the rate of pressure decay in memory 150. The calculated rate of pressure decay may be inclusive of a leak rate attributable to application of wound dressing 104; control unit 114 can determine the leak rate attributable to application of wound dressing 104 based on a duty cycle of pump 120 (as there may be no fluid in tubing 108) and remove the leak rate from the calculated rate of pressure decay.

In some embodiments, the therapy parameter(s) can be used by the caregiver as indications of therapy progression or need for a wound dressing replacement. The therapy parameter(s) may include a calculation of an exudate volume in the wound dressing and the wound to dressing fluid absorbance rate. In some embodiments, the therapy parameter(s) includes a moisture level, fluid level, fluid flow, or other parameter indicative of hydration or change in hydration of the wound dressing.

After calculation of an initial set of therapy parameters, control unit 114 can output the set of therapy parameters to at least one of the NPWT device or another remote electronic device (step 708). Outputting the therapy parameter(s) may include storing the therapy parameter(s) in memory 150 for later retrieval. Outputting the therapy parameter(s) may include comparing the therapy parameter to a predetermined threshold condition including at least one of a minimum threshold or a maximum threshold, and outputting an alert responsive to the therapy parameter(s) not satisfying the predetermined threshold condition.

Pump controller 152 can continue to control operation of pump 120 to perform therapy, by causing pump 120 to draw down pressure in wound dressing 104 to the predetermined target pressure, and executing a closed loop control of pump 120 based on the predetermined target pressure (step 710).

Subsequent to therapy parameter calculator 154 calculating the initial therapy parameters and pump controller 152 causing pump 120 to return wound dressing 104 to the predetermined target pressure negative pressure, control unit 114 can monitor for at least one of (1) expiration of a predetermined amount of time (step 712) or (2) a pressure change detected by pressure sensor(s) 126, 132 that is greater than a threshold pressure change (step 714). Responsive to detecting the at least one of (1) the pressure change detected by pressure sensor(s) 126, 132 that is greater than a threshold pressure change, such as the case of a fluid bolus entering the dressing, or (2) the expiration of a predetermined amount of time, control unit 114 can repeat steps 704 through 710, causing the sealable aperture to open, calculating updated therapy parameters such as rate of pressure decay and fluid absorbent capacity of wound dressing 104, and outputting those therapy parameters to a remote electronic device. In some embodiments, therapy parameter calculator 154 calculates updated values of therapy parameters and stores these values in memory 150.

In some embodiments, operation of the NPWT device is modified using the therapy parameter(s). The therapy parameter(s) may include a calculated pressure. A difference can be calculated between the calculated pressure and a target pressure value, and the pressure applied by the wound dressing to the wound (using the NPWT device) can be modified to reduce the difference.

In some embodiments, a level of moisture in the wound dressing is detected. The level of moisture can be compared to a predetermined threshold moisture condition including at least one of a minimum moisture threshold or a maximum moisture threshold. An alert can be outputted responsive to the level of moisture not satisfying the predetermined threshold moisture condition.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A negative pressure wound therapy system, comprising:
   at least one sensor coupled to a wound dressing for a wound of a patient, the at least one sensor configured to detect a pressure in the wound dressing;
   a sealable aperture coupled to the at least one sensor; and
   a processing circuit configured to:
     open the sealable aperture to induce a pressure change between the pressure in the wound dressing and atmospheric pressure;
     calculate a rate of pressure decay in the wound dressing based on the pressure change; and
     calculate a wound dressing fluid absorbent capacity based on the rate of pressure decay using a plurality of calibrations relating fluid volumes in the wound dressing with pressure decay; and
   a communications circuit coupled to the processing circuit, the communications circuit configured to transmit data to a remote electronic device.

2. The negative wound therapy system of claim 1, wherein the negative pressure wound therapy system is canister-free.

3. The negative wound therapy system of claim 1, wherein the processing circuit is configured to open the sealable aperture to calculate the wound dressing fluid absorbent capacity at start up.

4. The negative pressure wound therapy system of claim 1, wherein the processing circuit is configured to store the pressure change over time.

5. The negative pressure wound therapy system of claim 4, wherein the processing circuit is further configured to calculate and store the rate of pressure decay based on the stored pressure change over time.

6. The negative pressure wound therapy system of claim 5, wherein the processing circuit is further configured to calculate the wound dressing fluid absorbent capacity based on the stored rate of pressure decay.

7. The negative pressure wound therapy system of claim 1, wherein the communications circuit is further configured to transmit the wound dressing fluid absorbent capacity to the remote electronic device responsive to at least one of (1) expiration of a predetermined time interval or (2) a request.

8. The negative pressure wound therapy system of claim 1, wherein the processing circuit is further configured to compare the wound dressing fluid absorbent capacity to a predetermined threshold condition including at least one of a minimum threshold or maximum threshold, and output an alert to the remote electronic device responsive to the wound dressing fluid absorbent capacity not satisfying the predetermined threshold condition.

9. The negative pressure wound therapy system of claim 1, wherein the processing circuit is further configured to calculate an exudate volume in the wound dressing based on the wound dressing fluid absorbent capacity.

10. The negative pressure wound therapy system of claim 9, wherein the communications circuit is further configured to transmit the exudate volume in the wound dressing to the remote electronic device responsive to at least one of (1) expiration of a predetermined time interval or (2) a request.

11. The negative pressure wound therapy system of claim 1, wherein the processing circuit is further configured to calculate a wound to dressing fluid absorbance rate based on the wound dressing fluid capacity.

12. The negative pressure wound therapy system of claim 11, wherein the communications circuit is further configured to transmit the wound to dressing fluid absorbance rate to the remote electronic device responsive to at least one of (1) expiration of a predetermined time interval or (2) a request.

13. The negative pressure wound therapy system of claim 1, wherein the processing circuit is further configured to open the sealable aperture responsive to at least one of (1) expiration of one or more predetermined time intervals subsequent to start up or (2) detecting a pressure change greater than a threshold pressure change.

14. The negative pressure wound therapy system of claim 13, wherein the processing circuit is further configured, each time the sealable aperture is opened, to calculate an updated rate of pressure decay and an updated wound dressing fluid absorbent capacity.

15. The negative pressure wound therapy system of claim 14, wherein the processing circuit is further configured to compare the updated wound dressing fluid absorbent capacity to a predetermined threshold condition including at least one of a minimum threshold or maximum threshold, and output an alert to the remote electronic device responsive to the updated wound dressing fluid absorbent capacity not satisfying the predetermined threshold condition.

16. The negative pressure wound therapy system of claim 14, wherein the processing circuit is configured to calculate an updated exudate volume in the wound dressing based on the updated wound dressing fluid absorbent capacity.

17. The negative pressure wound therapy system of claim 13, wherein the processing circuit is configured to calculate an updated wound to dressing fluid absorbent rate based on the updated wound dressing fluid absorbent capacity.

18. The negative pressure wound therapy system of claim 1, wherein the at least one sensor is coupled to the processing circuit and mounted in a therapy unit.

19. The negative pressure wound therapy system of claim 1, wherein the sealable aperture consists of a two-way controllable exhaust valve.

20. The negative pressure wound therapy system of claim 1, wherein the sealable aperture consists of a controllable pump containing an internal leak.

21. A method, comprising:
   detecting, by at least one sensor of a therapy unit, a pressure in a wound dressing;
   opening, by the processing circuit, a sealable aperture responsive to at least one of (1) start up, (2) expiration of one or more predetermined time intervals subsequent to start up, or (3) detecting a pressure change greater than a threshold pressure change, to induce a pressure change based on the pressure in the wound dressing to atmospheric pressure;
   calculating, by the processing circuit, a rate of pressure decay in the wound dressing based on the pressure change;
   calculating, by the processing circuit, a wound dressing fluid absorbent capacity using a plurality of calibrations relating fluid volumes in the wound dressing with pressure decay; and
   communicating, by the therapy unit, the wound dressing fluid absorbent capacity to a remote electronic device.

22. The method of claim 21, further comprising comparing, by the processing circuit, the wound dressing fluid absorbent capacity at start up to a predetermined threshold condition including at least one of a minimum threshold or maximum threshold, and outputting an alert to the remote electronic device responsive to the wound dressing fluid absorbent capacity not satisfying the predetermined threshold condition.

23. The method of claim 21, further comprising calculating, by the processing circuit, an exudate volume in the wound dressing based on the wound dressing fluid absorbent capacity.

24. The method of claim 23, further comprising communicating, by the therapy unit, the exudate volume in the wound dressing to the remote electronic device at a predetermined time interval or responsive to a request.

25. The method of claim 21, further comprising calculating, by the processing circuit, a wound to dressing fluid absorbent rate based on the wound dressing fluid absorbent capacity.

26. The method of claim 25, further comprising communicating, by the therapy unit, the wound to dressing fluid absorbent rate to the remote electronic device at a predetermined time interval or responsive to a request.

27. The method of claim 21, further comprising opening, by the processing circuit, the sealable aperture at predetermined time intervals subsequent to start up or responsive to detecting a rapid pressure change.

28. The method of claim 27, further comprising calculating, by the processing circuit, an updated wound dressing fluid absorbent capacity each time the processing circuit opens the sealable aperture.

29. The method of claim 28, further comprising comparing, by the processing circuit, the updated wound dressing fluid absorbent capacity to a predetermined threshold condition including at least one of a minimum threshold or maximum threshold, and outputting an alert to the remote electronic device responsive to the wound dressing fluid absorbent capacity not satisfying the predetermined threshold condition.

30. The method of claim 29, further comprising calculating, by the processing circuit, an updated exudate volume in the wound dressing based on the updated wound dressing fluid absorbent capacity.

31. The method of claim 30, further comprising calculating, by the processing circuit, an updated wound to dressing fluid absorbent rate based on the updated wound dressing fluid absorbent capacity.

32. A negative pressure wound therapy system, comprising:
   a wound dressing for a wound of a patient, the wound dressing including a super absorbent material forming at least thirty percent of a volume of the wound dressing;
   at least one sensor coupled to the wound dressing, the at least one sensor configured to detect a pressure in the wound dressing;
   a sealable aperture coupled to the at least one sensor; and
   a processing circuit configured to:
      open the sealable aperture to induce a pressure change between the pressure in the wound dressing and atmospheric pressure;
      calculate a rate of pressure decay in the wound dressing based on the pressure change; and
      calculate a wound dressing fluid absorbent capacity based on the rate of pressure decay using a plurality of calibrations relating fluid volumes in the wound dressing with pressure decay; and
   a communications circuit coupled to the processing circuit, the communications circuit configured to transmit data to a remote electronic device.

33. A non-transitory computer-readable medium storing computerexecutable instructions that when executed by one or more processors cause the one or more processors to:
   open a sealable aperture to induce a pressure change based on the pressure in a wound dressing to atmospheric pressure;
   receive a series of pressure data corresponding to the pressure change in the wound dressing based on at least one sensor, the at least one sensor coupled to the wound dressing;
   calculate a wound dressing fluid absorbent capacity corresponding to the pressure data using a plurality of calibrations relating fluid volumes in the wound dressing with pressure data; and
   output the wound dressing fluid absorbent capacity to a remote electronic device.

* * * * *